United States Patent [19]
Crane et al.

[11] Patent Number: 5,604,112
[45] Date of Patent: Feb. 18, 1997

[54] METHOD FOR DETECTING THE CARDIOTOXICITY OF COMPOUNDS

[75] Inventors: Paul D. Crane, Sudbury; Cesare Orlandi, Burlington, both of Mass.

[73] Assignee: The Dupont Merck Pharmaceutical Company, Wilmington, Del.

[21] Appl. No.: 23,396

[22] Filed: Feb. 26, 1993

[51] Int. Cl.$^6$ ........................................................ C12Q 1/02
[52] U.S. Cl. .................................. 435/29; 435/32; 435/35; 435/39; 435/968; 436/172
[58] Field of Search ........................ 435/4, 244, 29, 435/968, 39, 32, 35, 975; 436/172, 800, 811, 1; 128/695, DIG. 3, 695 A

[56] References Cited

PUBLICATIONS

Morrison and Boyd "Organic Chemistry," 3rd Edition 1975 pp. 1059–1062.
Orlandi, et al. JACC 19: Abstract No. 249 A. 1992.
Nadakavukaren, et al. Cancer Research vol. 45 pp. 6093–6099 1985.
Savi, et al. Eur. J. Nucl. Med. 15:597–600 (1989).
Bachur et al., "NADPH Cytochrome P–450 Reductase Activation of Quinone Anticancer Agents to Free Radicals", *Proc. Natl. Acad. Sci. U.S.A.*, 76: 954–957 (1979).
Carvalho et al., "Subcellular Distribution and Analysis of Technetium–99m–MIBI in Isolated Perfused Rat Hearts", *J. Nucl. Med.* 33: 1516–1521 (1992).
Chen, "Mitochondrial Membrane Potential in Living Cells", *Ann. Rev. Cell. Biol.* 4: 155–181 (1988).
Crane et al., "Calcium Causes Release of Tc–99m–Sestamibi from Cardiac Mitochondria", *Circulation* 82: III–486 (1990) Abstract.
Crane et al., "Cardiac Retention of Tc–99m–Sestamibi is Related to Mitochondrial Viability", *J. Nucl. Med.* 32: 957 (1991).
Crane et al., "Effect of Mitochondrial Viability and Metabolism on Technetium–99m–Sestamibi Myocardial Retention", *Eur. J. Nucl. Med.* 20: 20–25 (1993).
Delmon–Moingeon, et al., "Uptake of the Cation Hexakis(2–methoxyisobutylisonitrile)–Technetium–99m by Human Carcinoma Cell Lines in Vitro", *Cancer Research*, 50: 2198–2202 (1990).
Duarte–Karim, "Affinity of Adriamycin to Phospholipids: A Possible Explanation for Cardiac Mitochondrial Lesions", *Biochem. Biophys. Res. Commun.*, 71: 658–663 (1976).
Gosalvez et al, "Effects of Anticancer Agents on the Respiration of Isolated Mitochondria and Tumor Cells", *Eur. J. Cancer*, 10: 567–574 (1974).
Goodman and Hochstein, "Generation of Free Radicals and Lipid Peroxidation by Redox Cycling of Adriamycin and Daunomycin", *Biochem. Biophys. Res. Commun.*, 77: 797–803 (1977).
Haugland, R. P., *Handbook of Fluorescent Probes and Research Chemicals*, (Molecular Probes, Inc.) 145–148 (1989).
March, ed., *Advanced Organic Chemistry*, 3rd ed., (John Wiley & Sons, Inc., NY, NY, 369–370, 429–430, 934, 1107–1108 (1985).
Mimnaugh et al, "The Effects of Adriamycin in Vitro and in Vivo on Hepatic Microsomal Drug–Metabolizing Enzymes: Role of Microsomal Lipid Peroxidation", *Toxicol. Appl. Pharmacol.*, 61: 313–315 (1981).
Moore et al, "Inhibition of the Cardiac Mitochondrial Calcium Pump by Adriamycin in Vitro", *Biochem. Med.*, 18: 131–138 (1977).
Nadakavukaren et al., "Increased Rhodamine 123 Uptake by Carcinoma Cells", *Cancer Res.*, 45: 6093–6099 (1985).
Orlandi et al., "Doxorubicin Causes Release of Tc–99m–Sestamibi from Cardiac Mitochondria", *JACC* 19: 249A (1992).
Tritton, "Cell Surface Actions of Adriamycin", *Pharmac. Ther.* 49: 293–309 (1991).

*Primary Examiner*—Leslie Wong
*Attorney, Agent, or Firm*—Gerald J. Boudreaux; David H. Vance

[57] ABSTRACT

The present invention provides methods of testing the cardiotoxicity of compounds and kits useful for the same.

28 Claims, No Drawings

METHOD FOR DETECTING THE CARDIOTOXICITY OF COMPOUNDS

FIELD OF THE INVENTION

This invention relates, inter alia, to the use of labeled isonitriles for testing the cardiotoxicity of compounds.

BACKGROUND OF THE INVENTION

The use of antimitotic agents as well as other drugs, is limited by their cardiotoxic action. Cardiotoxicity can be manifested by tachycardia, arrhythmias, dyspnea, hypotension, and congestive heart failure that is unresponsive to digitalis. The mortality rate associated with such cardiotoxicity is in excess of 50%. The use of several important therapeutic agents, including anti-cancer drugs such as the anthracycline antibiotic, adriamycin (doxorubicin), is hampered by these cardiotoxic effects.

The mechanism(s) of cardiac toxicity is complex. Several hypotheses have been formulated, including reduction of adriamycin to form a free radical (Bachur et al., 1977, *Proc. Natl. Acad. Sci. U.S.A.*, 76:954–957) with subsequent generation of activated oxygen species (Goodman and Hochstein, 1977, *Biochem. Biophys. Res. Commun.*, 77: 797–803) and lipid peroxidation (Mimnaugh et al., 1981, *Toxicol. Appl. Pharmacol.*, 61: 313–315); alterations of mitochondrial respiration (Gonsalvez et al, 1974, *Eur. J. Cancer*, 10: 567–574) or $Ca^{++}$ metabolism (Moore et al, 1977, *Biochem. Med.*, 18: 131–138); and interaction with the mitochondrial lipid cardiolipin (Duarte-Karim, 1976, *Biochem. Biophys. Res. Commun.*, 71: 658–663). It is possible that the mechanism is "multimodal", with several parallel actions being responsible (Tritton, 1991, *Pharmac. Ther.* 49:293–309).

Evaluation of possible cardiotoxicity is an important and necessary step during the development of new therapeutics and other agents. However, reliable, easy, and/or inexpensive screening methods to assess cardiotoxicity are lacking at the present time.

An assay is greatly needed to assess the potential cardiotoxicity of drugs and other compounds. The present invention is directed to this, as well as other, important ends.

SUMMARY OF THE INVENTION

The present invention provides a method of testing for cardiotoxicity of a compound comprising the steps of:
(a) labeling cells with a labeled lipophilic cationic agent;
(b) homogenizing the labeled cells to provide a cell homogenate;
(c) incubating the cell homogenate with the compound to be tested;
(d) obtaining a mitochondrial fraction from the cell homogenate; and
(e) measuring the amount of labeled lipophilic cationic agent in the mitochondrial fraction, wherein a decrease of labeled lipophilic cationic agent in the mitochondrial fraction as compared to a control not incubated with the compound to be tested is indicative of cardiotoxic effect caused by the compound.

The present invention also provides a method of testing for cardiotoxicity of a compound wherein the labeled lipophilic cationic agent is a labeled isonitrile having the formula $[M(CN-R)_6]$ where M is a label and R is a straight, branched, or cyclic $C_1-C_{10}$ alkyl group.

The present invention also provides a method of testing for cardiotoxicity of a compound wherein the labeled lipophilic cationic agent is a labeled ether-substituted isonitrile having the formula $[M(CN-A-O-R)_6]$ where M is a label, A is a straight or branched chain alkyl group and R is a straight or branched chain alkyl group, provided that the total number of carbon atoms in A plus R is 4 to 6, further provided that when the total number of carbon atoms in A plus R is 6, then the carbon atom alpha to the isonitrile group is a quaternary carbon, and still further provided that A is not $(CH_2)_3$.

The present invention also provides a kit for testing the cardiotoxicity of a compound comprising, in a first vial, a sterile mixture of a lipophilic cationic agent, and a biocompatible buffer, which mixture (prior to any lyophilization) has a pH ranging from about 7.0 to about 7.4 pH units, and, in a second vial, a radiolabeling agent.

DETAILED DESCRIPTION OF THE INVENTION

It has been discovered, inter alia, that the response of intramitochondrial Tc-99m-sestamibi, and other labeled lipophilic agents having a cationic charge, to mitochondrial perturbation provides a mechanism to test for cardiotoxicity of drugs and other compounds. Thus, in accordance with the present invention, methods are provided to determine the cardiotoxicity of drugs based upon the response of intramitochondrial lipophilic agents having cationic charge such as isonitriles and more particularly ether-substituted isonitriles such as Tc-99m-sestamibi.

Labeled isonitriles having the formula $[M(CN-R)_6]$ where M is a label and R is a straight, branched or cyclic $C_1-C_{10}$ alkyl group are one preferred type of lipophilic cationic agent. Isonitriles encompassed by the present invention include, but are not limited to, acetonitrile, propionitrile, butyronitrile, valeronitrile, capronitrile, caprylonitrile, benzonitrile and tolunitrile. Preparation of such isonitriles is well known in the art, and is described, for example, in March, ed., *Advanced Organic Chemistry*, 3rd ed., (John Wiley & Sons, Inc., NY, N.Y., 1985), the disclosures of which are incorporated herein by reference in their entirety.

In still more preferred embodiments of the present invention the lipophilic cationic agent is an ether-substituted isonitrile generally have the formula:

wherein M is a label, A is a straight or branched claim alkyl group and R is a straight or branched chain alkyl group, provided that the total number of carbon atoms in A plus R is 4 to 6, further provided that when the total number of carbon atoms in A plus R is 6, then the carbon atom alpha to the isonitrile group is a quaternary carbon, and still further provided that A is not $(CH_2)_3$.

The ether-substituted isonitriles useful in methods of the present invention can be readily prepared by formylation of an alkyoxyamine of the general formula II to give the corresponding formamide III, followed by dehydration to the isonitrile I.

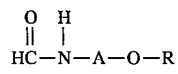

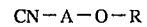

A variety of methods for the formylation and dehydration reactions are available in the literature and are well known to one skilled in the art of organic synthesis.

The amines II can be prepared by a variety of methods known to one skilled in the art. In particular, the amines can be prepared by opening of an aziridine IV with an alcohol in the presence of an acid catalyst to give a mixture of the two amines X and VI which can be separated by distillation.

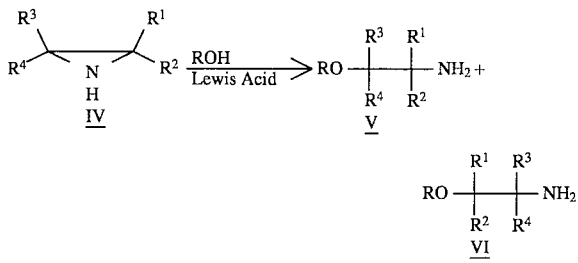

Alternatively, the amines can be prepared from alkyoxyesters VII wherein A' is a hydrocarbon of 2 or 3 carbon atoms. Formation of the amide VIII by reaction with ammonia or ammonium hydroxide, followed by reduction with lithium aluminum hydride or another reducing agent known to reduce amides affords the amine IX.

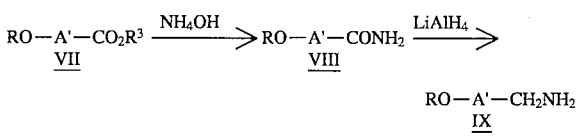

The amines II can also be prepared from the alkoxyesters X. Formation of the amide XI proceeds as described above. The amide XI is subjected to the Hofmann Rearrangement to provide the amine II.

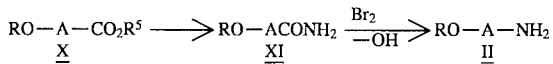

Alternatively, the ether isonitriles can be prepared from amino alcohols XII by first reacting with a formylating agent, such as ethyl formate or formic acetic annhydride, to form the formamide-formate XIII. Conversion of the formamide-formate to the isonitrile-formate XIV is accomplished as already described for the other formamides. Mild aqueous hydrolysis of the formate yields the isonitrile-alcohol XV which can then be alkylated under standard alkylating conditions such as using sodium hydride and methyl halide such as iodide.

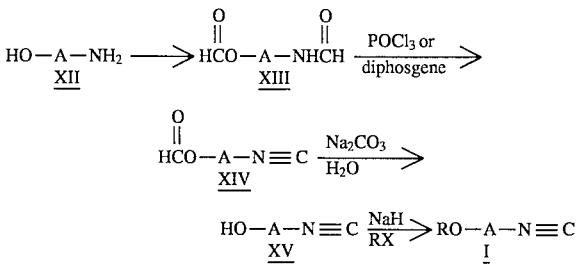

The ether-substituted isonitriles useful in methods of the present invention include, but are not limited to: $CNCH_2CH_2CH_2OCH_3$; $CNCH_2CH_2CH_2OCH_2CH_3$; $CNC(CH_2)OCH_2CH_3$; $CNC(CH_3)_2OCH_3$; $CNCH_2C(CH_3)_2OCH_3$; $CNC(CH_3)_2CH_2OCH_3$; $CNCH(CH_3)CH_2OCH_3$; $CNCH(CH_3)CH_2OCH_2CH_3$; $CNCH_2CH(CH_3)OCH_3$; $CNCH_2CH(CH_3)OCH_2CH_3$; $CNCH(CH_3)CH(CH_3)OCH_3$; $CNCH_2CH_2OCH(CH_3)_2$; $CNCH_2CH_2CH(CH_3)OCH_3$; $CNCH_2CH_2OCH(CH_3)_2$; $CNCH_2CH_2OCH_2CH_3$; $CNCH(CH_3)OCH(CH_3)_2$; $CNCH_2CH(CH_2CH_3)OCH_3$; $CNCH(CH_2CH_3)CH_2OCH_3$; $CNCH(CH_3)CH_2CH_2OCH_3$; $CNC(CH_3)_2CH_2CH_2OCH_3$.

Preferably, the ether-substituted isonitrile, $CNCH_2C(CH_3)_2OCH_3$ is utilized in some aspects of the present invention. These and other lipophilic cationic agents will be readily apparent to one skilled in the art once armed with the present disclosure. The requirements of such agents are, of course, that such agents are lipophilic (non-polar) and cationic (positively charged). These lipophilic cationic agents may be in a non-pyrogenic form (i.e. a form which is not produced by heating).

In accordance with the present invention, lipophilic cationic agents are preferably labeled. Radiolabeling and fluorescent lipophilic cationic labeling are two effective labeling strategies which may be useful for methods of the present invention.

Lipophilic cationic fluorescent labels include, but are not limited to dyes such as 1,1'-dihexadecyloxacarbocyanine perchlorate, 3,3'-dioctadecyloxacarbocyanine perchlorate, 1,1'-didodecyl-3,3,3',3'-tetramethylindocarbocyanine perchlorate, 1,1'-dihexadecyl-3,3,3',3'-tetramethylindocarbocyanine perchlorate, 1,1'-dioctadecyl-3,3,3',3'-tetramethylindocarbocyanine perchlorate, 1,1'-didocosanyl-3,3,3',3'-tetramethylindocarbocyanine perchlorate, 1,1'-dioctadecyl-3,3,3',3'-tetramethylindodicarbocyanine perchlorate, 3,3'-dioctadecylthiacarbocyanine perchlorate, octadecyl rhodamine B, N-4-(4-didecylaminostyryl)-N-methylpyridinium iodide, 1-(4-trimethylammoniumphenyl)-6-phenyl-1,3,5-hexatriene, p-toluenesulfonate, 6-palmitoyl-2(((2-(trimethyl)ammonium)ethyl)methylamino)naphthalene, 1-pyrenemethyltrimethylammonium iodide, 1-pyrenebutyltrimethylammonium bromide, 3-(9-anthracene)propyl trimethylammonium bromide, acridine orange-10-dodecyl bromide, acridine orange-10-nonyl bromide and rhodamine as disclosed by Haugland, R. P., *Handbook of Fluorescent Probes and Research Chemicals,* (Molecular Probes, Inc. 1989). In preferred embodiments of the present invention, the fluorescent label is a rhodamine label. Fluorescent labeling can be carried out by conventional means. The desired fluorescently labeled lipophilic cationic agents are easily isolatable and can be obtained in high yields by those skilled in the art. These and other fluorescent labels and methods of making and using the same are disclosed, for example, by Haugland, R. P., *Handbook of Fluorescent Probes and Research Chemicals,* (Molecular Probes, Inc. 1989) the disclosure of which is herein incorporated by reference in its entirety.

The lipophilic cationic agents can also be radiolabeled. Radiolabeling can generally be carried out by admixing the lipophilic cationic agent with a radionuclide (radioactive metal) in suitable media at temperatures from room temperature to reflux temperatures or even higher. Preferably, the radioactive metal has high specific activity and is conveniently available. Suitable radionuclides include, but are not limited to radioactive isotopes of carbon, hydrogen, iodine, technetium, ruthenium, cobalt, platinum, iron, osmium, iridium, tungsten, rhenium, chromium, molybdenum, manganese, nickel, rhodium, lead, niobium, and terbium such as C-14, H-3, I-125, Tc-99m, Tc-99, Ru-97, Cr-51, Co-57, Re-188, and Os-191. The desired radiolabeled lipophilic cationic agents are isolatable and can be obtained in high yields. In some cases the agent itself, such as an isonitrile, can act as a reducing agent thus eliminating the need for an additional reducing agent. Additional reducing agents, when required or desired to speed up the reaction, are well known to those skilled in the art. Examples of such well-known reducing agents include stannous salt, formamidine sulfinic acid, sodium dithionite, sodium bisulfite, hydroxylamine, ascorbic acid, and the like. The reaction is generally complete in from about 1 minute to about 2 hours, depending upon the particular reagents employed and the conditions used.

In the case of technetium isotopes such as, for example, Tc-99 or Tc-99m, and an isonitrile, the complex is preferably made by mixing an appropriate reducing agent (capable of reducing technetium in aqueous medium) and an appropriate ether-substituted isonitrile, then adding pertechnetate. Alternatively, an ether-substituted isonitrile and pertechnetate are mixed, then reductant added.

The technetium complexes prepared in accordance with this invention can also be prepared from preformed technetium complexes having oxidation states for technetium of, for instance, III, IV or V, by treated these preformed complexes with an excess of lipophilic cationic agent such as isonitrile under suitable conditions.

An excess of the lipophilic cationic agent, such as isonitrile, up to 100 fold molar excess or more, and an excess of reducing agent, can be used in the complexing reaction to ensure maximum yield from technetium. Following the reaction the desired complex can be separated from the reaction mixture, if required, for example by crystallization or precipitation or by conventional chromatography or ion exchange chromatography.

The labeled lipophilic cationic agent may be delivered to the cells to be labeled in a biocompatible buffer if desired. For instance, the labeled lipophilic cationic agent generally should be soluble in from about 0.5% to 1% saline when used for intravenous administration and should be free from any cytotoxic materials used during synthesis so as to avoid inconclusive cardiotoxicity results. Alternatively, the agent may be delivered to cell culture in cell culture medium.

As noted above, the lipophilic cationic agent of the present invention may be used to label cells. Heart tissue cells (cardiac cells) may be labeled in vivo, for example, by intravenous injection of laboratory animals such as mouse, rat, hamster, guinea pig, rabbit, pig and dog. In some embodiments of the present invention guinea pig heart tissue is selected. However, the selection of the source of heart tissue is based mainly on convenience since it is preferable that the injection can be made easily and that there by sufficient quantity of heart tissue for performance of the assay. Alternatively, cells to be labeled may be cultured cells having high negative membrane potential such as EJ (Nadakavukaren, et al., 1985, *Cancer Res.*, 45: 6093–6099), RT4 (ATCC#HTB2), SKBR3 (ATCC#HTB30) and MCF7 (ATCC#HTB22) cells. As used herein ATCC denoted the American Type Culture Collection, Rockville, Md.

In accordance with methods of the present invention, labeled lipophilic cationic agent is administered to the cells for from about 5 minutes to about 90 minutes. The specific activity of the label will generally dictate the amount of labeled lipophilic cationic agent used to label cells. High specific activity requires less lipophilic cationic agent, whereas lower specific activity will require addition of more lipophilic cationic agent. One skilled in the art will be able to appropriately adjust concentrations to suit any given situation. It should be noted, however, that extremely high concentrations of labeled lipophilic cationic agent should be avoided since this may cause cell toxicity from accumulation of cations within the cells. Thus, it is preferable that the label chosen have high specific activity.

Preferably, cells labeled in vivo are exposed to the lipophilic cationic agent for from about 5 to about 15 minutes. It has been found, for example, that at 4° C. by 10 minutes greater than 95% of Tc-99m-sestamibi in a cardiac homogenate is recovered in the mitochondrial fraction. Crane et al., *Eur. J. Nucl. Med.* 20:20–25 (1993), the disclosure of which is incorporated by reference herein in its entirety. Alternatively, cells in cell culture may be incubated with the label for a longer duration which may range from about 30 to about 90 minutes. However, one skilled in the art would be familiar with any variability associated with labeling cells and would be able to appropriately adjust labeling conditions to optimize labeling under any given set of conditions, such as in vivo, in vitro, etc.

Following labeling, heart tissue or cells from cell culture may be homogenized in buffer, preferably cold buffer, such as by use of a Polytron tissue grinder (Model PT 10/35, Brinkmann Instruments, Westbury, N.Y.) or other homogenizers which are commercially available such as hand held devices or house-hold blender types. It may be useful, in some instances, to mince tissue prior to homogenization.

The divalent cation concentration of buffers used in the methods of the present invention preferably should not exceed 10 µM. Tris buffer is preferred in some embodiments of the present invention. Hepes or phosphate buffers are also suitable.

Since cardiotoxicity has been found to be dose-related in some cases, cell homogenate labeled with labeled lipophilic cationic agents is preferably incubated with various concentrations of test compounds solutions in buffer. Test compounds include, but are not limited to anthracycline antibiotics such as daunorubicin, adriamycin (doxorubicin) and derivatives and analogs thereof. Of course any compound which has known or suspected cardiotoxic effect, including experimental drugs, may be tested using methods of the present invention.

Incubation is generally carried out at from about 20° C. to about 40° C. Preferably incubation is carried out in a shaking water bath at 37° C. One to 10 minutes is generally sufficient time for incubation to be complete. However, at these temperatures it may be preferable to limit incubation to no more than 5 minutes in order to limit release of the label from the control, since the homogenate may be rather labile. Thereafter, the mitochondrial pellet fraction is obtained by centrifugation in accordance with methods known in the art. The mitochondrial fraction contains the cellular mitochondria and may, if desired, contain other cellular components. Fractions are assayed for label. In accordance with some aspects of the present invention the label is radioactive and may be detected using, for example, a gamma well counter or liquid scintillation counter. In such cases, counts per minute are decay corrected to the counting time of the first sample and the percent of the radiolabeled lipophilic cationic agent from the cell homogenate which was recovered in the pellet is calculated using the formula:

$$\%=[(\text{cpm pellet})/(\text{cpm pellet}+\text{cpm supernatant})]\times 100.$$

Greater cardiotoxic effect causes increased loss of radiolabeled lipophilic cationic agent from the mitochondrial fraction (pellet) into the supernatant following incubation with the compound as can be seen, for example, in Example 1, Table 1.

In still other embodiments of the present invention the label is a fluorescent dye which can be detected with a fluorometer. The percent of the fluorescently labeled lipophilic cationic agent from the cell homogenate which is recovered in the pellet is calculated similar to the method given above based upon the intensity of signal measured in the mitochondrial pellet as compared to the supernatant.

The cardiotoxic effect of a compound is generally measured by comparison to a standard in which cells have not been treated with the compound being tested, thereby providing a baseline. Thus, where there is a statistically significant degree of label lost from the mitochondrial pellet into the supernatant as compared to a non-treated standard, some degree of cardiotoxicity is generally believed to be caused by the compound being tested.

Titration experiments may also be performed in accordance with methods of the present invention whereby an optimal dosage of a compound may be determined by testing of sequentially increasing dosages in accordance with methods of the invention.

The present invention is also directed to kits for testing the cardiotoxicity of a compound comprising, in a first vial, a sterile mixture of a lipophilic cationic agent and a biocompatible buffer, which mixture (prior to any lyophilization) has a pH ranging from about 7.0 to about 7.4 pH units, and, in a second vial, a radiolabeling agent. Selection of buffers, reducing agents, etc. which are suitable for a particular purpose will be evident to one skilled in the art and will be partially dictated by the cells to be labeled, the type of label, and the lipophilic cationic agent, etc. In some embodiments of the present invention, a reducing agent such as dithionite, which is effective at pH ranges from about 7.0 to about 7.4 pH units may preferably be included in the first vial mixture. In some embodiments of the present invention kits of the present invention are non-pyrogenic (i.e. do not cause heat which might lead to inflammation at the site of injection). Conventional kit components such as buffering agents, antibacterial agents, stabilizing agents and excipients are also encompassed in kits of the present invention. Such components are well known in the art and are discussed, for example, in *The United States Pharmacopeia—The National Formulary*, 22nd Revision, Jan. 1, 1990, Mack Publishing Company, Easton, Pa., *Remington's Pharmaceutical Sciences*, Gennaro, A. R., ed., Mack Publishing Company, Easton, Pa. (1985), the disclosures of each of which are hereby incorporated herein by reference in their entirety.

Although not intending to be bound by any theory of operation, it is believed that alterations in mitochondrial calcium metabolism is a primary event in the pathogenesis of cardiotoxicity. A labeled lipophilic agent having a positive (cationic) charge as described herein may be useful in assessing such cardiotoxicity because it allows examination of such alterations. Specifically, the lipophilicity of the agent may permit its diffusion across cell membranes during mitochondrial loading, while the cationic charge may provide a trapping mechanism for the agent within the mitochondria as a result of the negative membrane potential of the mitochondrial membrane. However, drug induced perturbation of mitochondria calcium metabolism has been found to cause release of lipophilic cationic agents from the mitochondria, which allows the compounds of the present invention to act as agents for the detection of cardiotoxicity.

The following examples are merely illustrative of the present invention and should not be considered as limiting the scope of the invention in any way. These examples and equivalents thereof will become more apparent to those versed in the art in light of the present disclosure, and the accompanying claims.

Example 1, as set forth below, is an actual example. Example 2, as set forth below, is a prophetic example.

EXAMPLES

Example 1

Male Hartley guinea pigs (300–550 g) were obtained from Elm Hill Breeding Laboratories and maintained on Purina #5025 chow (ad libitum) until the day of the study. A solution of Tc-99m-sestamibi was prepared as described in Crane, et al., *Eur. J. Nucl. Med.*, 20:20–25 (1993), the disclosure of which is incorporated herein by reference in its entirety. The guinea pigs were then anesthetized with sodium pentobarbital (28 mg/kg, intraperitoneally). The animals were restrained on a surgical board, and the jugular vein was surgically exposed. The Tc-99m-Sestamibi solution was taken up to the 0.1 ml mark into a 1 ml syringe, fitted with a 30 gauge needle. The Tc-99m activity of the syringe solution was determined in a Capintec radioisotope calibrator. The solution of Tc-99m-Sestamibi was then administered to the guinea pigs via the jugular vein. The site of injection was then swabbed with a cotton tip applicator, and the Tc-99m activity remaining in the syringe, needle and swab was determined as described above. The injected dose was calculated by subtraction of this residual amount from the syringe activity before injection.

The animals were euthanized by decapitation at 10 minutes after injection, and the now Tc-99m-Sestamibi-labeled hearts were rapidly excised. The atrial tissue was dissected and discarded. The remaining septal and ventricular tissues were removed and minced with a scalpel. The minced cardiac tissue was weighed and placed in 50 ml polycarbonate centrifuge tubes with 10 volumes of cold 20 mM Tris-HCl, pH 7.4. The tissue was homogenized, and one ml aliquots of the homogenate were then transferred to 1.5 ml polypropylene microcentrifuge tubes, and placed on ice.

The microfuge tubes containing 1 ml of Tc-99m-Sestamibi labeled cardiac homogenate were incubated without (control) or with adriamycin, a known cardiotoxic drug, as described in Table 1. Various concentrations of adriamycin (0.02–1.44 mM) were achieved by the addition of 0.01–0.08 ml of concentrated adriamycin in distilled water. These samples, along with controls without adriamycin were vortexed and incubated at 37° C. in a shaking water bath for 5 min. The tubes were then centrifuged at 12,000 rpm (~10,000 g) in a Sorvall microspin 24S centrifuge for 10 min in a cold room (4° C.) to obtain the mitochondrial fraction. The supernatants were separated from the pellets, and both fractions were assayed for Tc-99m activity in a Pharmacia LKB gamma well counter. The percentage of Tc-99m-Sestamibi in the mitochondrial pellet fraction was then calculated for each cardiac tissue sample as follows:

$$\% = [(\text{cpm pellet})/(\text{cpm pellet} + \text{cpm supernatant})] \times 100$$

The % calculated above for the adriamycin-treated cardiac tissue was then subtracted from the % calculated above for the control (68.6%±1.95% retained) to achieve the % of Tc-99m-Sestamibi released from the mitochondrial pellet fraction as a result of adriamycin treatment. The results are set forth in Table 1 below. As the data indicates, the known dose-dependent cardiotoxicity of adriamycin correlates with the release of the Tc-99m-Sestamibi compound from the mitochondrial pellet fraction.

TABLE 1

| Adriamycin (mM) | Tc-99m-Sestamibi Released (%) | St. Dev. (%) |
|---|---|---|
| 0.02 | 5.5 | 1.9 |
| 0.05 | 8.6 | 0.7 |
| 0.10 | 14.5 | 1.3 |
| 0.14 | 23.9 | 0.7 |
| 0.19 | 28.7 | 0.6 |
| 0.24 | 11.6 | 4 |
| 0.48 | 21.4 | 5.6 |
| 0.96 | 36.8 | 5.7 |
| 1.44 | 47.3 | 7.2 |

Example 2

Cells with known high negative membrane potential, e.g. EJ, RT4 (Chen, 1988, *Ann. Rev. Cell. Biol.*) SKBR3 (Delmon-Moingeon, et al., 1990, *Cancer Research*, 50:2198–2202) or MCF7 (Nadakavukaren et al., 1985, *Cancer Research*, 45: 6093–6099) are grown to confluence in culture, trypsinized, washed and brought to a concentration of $10^8$ cells in 50 ml of serum free medium. The disclosure of each of these references are incorporated by reference herein in their entirety. The cells are transferred to a T75 flask and incubated with rocking for 2 hours at 37° C. to allow equilibration from trypsinization. The cells are then pelleted in a 50 ml centrifuge tube. Fifty µCi of Tc-99m-sestamibi is then added and the cells are incubated for 60 min at 37° C. The cells are homogenized in a Polytron tissue grinder and the tube is kept on ice throughout the process. Homogenate aliquots (1.0 ml) are then assayed with a compound to be tested for cardiotoxicity, as described in Example 1. The cardiotoxic effect of the test drug is expressed as the percent of Tc-99m-Sestamibi released from the mitochondrial pellet fraction as a result of treatment with the test compound.

The disclosures of any and all of the references cited herein are incorporated by reference herein in their entirety.

Various modifications of the invention in addition to those shown and described herein will be apparent to those skilled in the art from the foregoing description. Such modifications are also intended to fall within the scope of the appended claims.

What is claimed is:

1. A method of testing for cardiotoxicity of a compound comprising the steps of:
    labeling cells having a negative membrane potential with a labeled lipophilic cationic agent;
    homogenizing the labeled cells to provide a cell homogenate;
    incubating the cell homogenate with the compound to be tested;
    obtaining a mitochondrial fraction from the cell homogenate;
    measuring the amount of labeled lipophilic cationic agent in the mitochondrial fraction.

2. The method of claim 1 wherein the cells are labeled in vivo by intravenous injection of laboratory animals of the labeled lipophilic cationic agent.

3. The method of claim 1 wherein the cells are labeled in vitro by administration of the labeled lipophilic cationic agent to the cells.

4. The method of claim 1 wherein the cells are EJ, RT4, SKBR3 or MCF7 cells.

5. The method of claim 1 wherein the lipophilic cationic agent is labeled with a radiolabel selected from the group consisting of a radioactive isotope of carbon, hydrogen, iodine, technetium, ruthenium, cobalt, platinum, iron, osmium, iridium, tungsten, rhenium, chromium, molybdenum, manganese, nickel, rhodium, lead, niobium, and terbium.

6. The method of claim 5 wherein the radioactive isotope is selected from the group consisting of C-14, H-3, I-125, Tc-99m, Tc-99, Ru-97, Cr-51, Co-57, Re-188, and Os-191.

7. The method of claim 6 wherein the radioactive isotope is Tc-99m.

8. The method of claim 1 wherein the lipophilic cationic agent is labeled with a cationic lipophilic dye.

9. The method of claim 8 wherein the dye is rhodamine.

10. A method of testing for cardiotoxicity of a compound comprising the steps of:
    labeling cells having a negative membrane potential with a labeled isonitrile having the formula where M is a label and R is a straight, branched, or cyclic chain $C_1$–$C_{10}$ alkyl group;
    homogenizing the labeled cells to provide a cell homogenate;
    incubating the cell homogenate with the compound to be tested;
    obtaining a mitochondrial fraction from the cell homogenate;
    measuring the amount of labeled isonitrile in the mitochondrial fraction.

11. The method of claim 10 wherein the cells are labeled in vivo by intravenous injection of the labeled isonitrile.

12. The method of claim 10 wherein the cells are labeled in vitro by administration of the labeled isonitrile to the cells.

13. The method of claim 10 wherein the cells are EJ, RT4, SKBR3 or MCF7 cells.

14. The method of claim 10 wherein the labeled isonitrile is labeled with a radiolabel selected from the group consisting of a radioactive isotope of carbon, hydrogen, iodine, technetium, ruthenium, cobalt, platinum, iron, osmium, iridium, tungsten, rhenium, chromium, molybdenum, manganese, nickel, rhodium, lead, niobium, and terbium.

15. The method of claim 14 wherein the radioactive isotope is selected from the group consisting of C-14, H-3, I-125, Tc-99m, Tc-99, Ru-97, Cr-51, Co-57, Re-188, and Os-191.

16. The method of claim 15 wherein the radioactive isotope is Tc-99m.

17. The method of claim 10 wherein the lipophilic cationic agent is labeled with a cationic lipophilic dye.

18. The method of claim 17 wherein the dye is rhodamine.

19. A method of testing for cardiotoxicity of a compound comprising the steps of:
    labeling cells having a negative membrane potential with a labeled ether-substituted isonitrile having the formula wherein M is a radionuclide, A is a straight or branched chain alkyl group and R is a straight or branched chain alkyl group, provided that the total number of carbon atoms in A plus R is 4 to 6, further provided that when the total number of carbon atoms in A plus R is 6, that the carbon atom alpha to the isonitrile group is a quaternary carbon, and still further provided that A is not $(CH_2)_3$;
    homogenizing labeled cells to provide a cell homogenate;
    incubating the cell homogenate with the compound to be tested;
    obtaining a mitochondrial fraction from the cell homogenate; and measuring the amount of labeled ether-substituted isonitrile released from the mitochondrial fraction.

20. The method of claim 19 wherein the cells are labeled in vivo by intravenous injection of laboratory animals of the labeled ether-substituted isonitrile.

21. The method of claim 19 wherein the cells are labeled in vitro by administration of the labeled ether-substituted isonitrile to the cells.

22. The method of claim 19 wherein the cells are EJ, RT4, SKBR3 or MCF7 cells.

23. The method of claim 19 wherein the ether-substituted isonitrile is labeled with a radiolabel selected from the group consisting of a radioactive isotope of carbon, hydrogen, iodine, technetium, ruthenium, cobalt, platinum, iron, osmium, iridium, tungsten, rhenium, chromium, molybdenum, manganese, nickel, rhodium, lead, niobium, and terbium.

24. The method of claim 23 wherein the radioactive isotope is selected from the group consisting of C-14, H-3, I-125, Tc-99m, Tc-99, Ru-97, Cr-51, Co-57, Re-188, and Os-191.

25. The method of claim 24 wherein the radioactive isotope is Tc-99m.

26. The method of claim 19 wherein the lipophilic cationic agent is labeled with a cationic lipophilic dye.

27. The method of claim 26 wherein the dye is rhodamine.

28. The method of claim 19 wherein the ether-substituted isonitrile is $CNCH_2C(CH_3)_2OCH_3$.

* * * * *